United States Patent [19]
Salce et al.

[11] Patent Number: 5,441,729
[45] Date of Patent: Aug. 15, 1995

[54] LOTION FOR REDUCTION OF POST PERMANENT WAVE ODORS

[75] Inventors: Ludwig Salce, Greenwich; Ronald F. Verdi, Norwalk, both of Conn.

[73] Assignee: Conair Corporation, Stamford, Conn.

[21] Appl. No.: 194,915

[22] Filed: Feb. 14, 1994

[51] Int. Cl.$^6$ ............................ A61K 7/06; A61K 7/09
[52] U.S. Cl. .................... 424/70.2; 424/70.5; 424/70.51; 514/974; 132/204; 132/205
[58] Field of Search ............... 424/71, 72, 70, 70.2, 424/70.5, 76.21, 70.51; 514/974; 132/202, 204, 205

[56] References Cited

U.S. PATENT DOCUMENTS

| | | | |
|---|---|---|---|
| 4,560,554 | 12/1985 | Kubo | 424/71 |
| 4,675,181 | 6/1987 | Kamiishi | 424/72 |
| 4,834,971 | 5/1989 | Klenk | 424/71 |
| 5,051,252 | 9/1991 | Scultz | 424/72 |

Primary Examiner—Thurman K. Page
Assistant Examiner—Sally Gardner
Attorney, Agent, or Firm—Haynes N. Johnson

[57] ABSTRACT

Post permanent wave hair odor is reduced by treating the hair fiber with an aqueous bicarbonate/carbonate salt solution and then with an acidic aqueous solution. After allowing sufficient time for this lotion to penetrate the fiber, the acidic aqueous solution is directly applied to the fiber so that a reaction with the bicarbonate/carbonate salts occurs. This reaction results in the formation of gaseous carbon dioxide. Evolution of this gas from deep within, as well as the surface, of the fiber serves to release any trapped volatile malodorous mercaptans and byproducts.

8 Claims, No Drawings

LOTION FOR REDUCTION OF POST PERMANENT WAVE ODORS

FIELD OF THE INVENTION

This invention relates to the field of permanent waving of hair and, in particular, to a lotion and method for reducing or eliminating the so-called "post-perm odor" which often occurs as a result of permanent waving.

BACKGROUND OF THE INVENTION

The procedure for permanently altering the contour of keratin fiber in hair is a two stage process. Cleavage of the cystine disulfide bond is the first step (i.e., reduction) while reforming these bonds, usually in a new configuration, by treating the reduced fiber with an oxidizing agent (i.e., neutralizer) is the second step.

Permanent waving of human hair is achieved by winding the fiber onto perm rods during this reduction and neutralization procedure. If performed correctly, this action will place the fiber under some stress. A waving lotion, usually consisting of a water soluble mercaptan (i.e., salts and esters of thioglycolic acid, cysteine, cysteamine, etc.), is then applied to the hair. The pH of this lotion normally can vary from pH 6.5 to pH 9.9. Under these conditions, the cystine disulfide bonds are cleaved (i.e., reduced) and fiber stress is removed by molecular rearrangement of the polymeric keratin structure. Once the new configuration is achieved, the fiber is treated with an oxidizing agent such as hydrogen peroxide, sodium bromate, or sodium chlorite, to "lock" the fiber into the newly formed configuration.

Reducing reagents can also be used to straighten curly hair; that is, the curl stress is removed by reduction of the hair followed by brushing and/or combing until the curl is relaxed and the fiber is in the straight configuration. The fiber is then neutralized to maintain the new "curl-less" shape. Sulfites and bisulfites, operating through a different chemical sequence of reactions, have also been utilized to cleave keratin disulfide bonds and permanently alter the fiber structure.

Low molecular weight mercaptans are foul smelling organic molecules that often contain malodorous impurities. When hair fibers are treated with these chemicals during the reduction stage, some of the mercaptans, together with impurities and byproducts formed by the various chemical reactions occurring are trapped into the porous keratin fiber structure. Release of these residual malodorous chemicals is responsible for the post-perm obnoxious odors. In general, the more porous the hair fiber, the more retentive the malodors. These malodors often linger and remain in the fiber even after several shampoo treatments.

BRIEF SUMMARY OF THE INVENTION

It has now been found that if the reduced hair fiber is rinsed with water, treated with a bicarbonate/carbonate "flow lotion" and then with an acidic aqueous solution, the fibers become relatively free of post perm malodors. A "flow lotion" is described, for this discussion, as a lotion containing a water-soluble carbonate and/or a bicarbonate salt that is applied after fiber reduction but before the oxidation step (i.e., neutralization).

In accordance with the present invention, a "flow lotion" composed of a 0.1 to 50% solution of a water soluble bicarbonate/carbonate salt is applied to previously reduced hair fiber. After allowing sufficient time for this lotion to penetrate the fiber, an acidic aqueous solution is directly applied to the fiber so that a reaction with the bicarbonate/carbonate salts occurs. This reaction results in the formation of gaseous carbon dioxide. Evolution of this gas from deep within, as well as the surface, of the fiber serves to release trapped volatile malodorous mercaptans and byproducts. This action reduces post perm odors caused by these chemicals being "trapped" in the fiber. It is believed that the odor absorbing properties of bicarbonates/carbonates may also aid in the removal of these odors.

It has been found that acidification and neutralization (i.e., oxidation) can be combined in one step when acidic hydrogen peroxide is used as the oxidant. This eliminates the need for a separate acidifying lotion. Hence, one can remove malodorous volatile components responsible for obnoxious post-perm hair fiber odor while reoxidizing the cysteine keratin bonds to cystine.

DETAILED DESCRIPTION OF THE INVENTION

The odors occurring after a permanent wave result from chemicals left in the hair. These can be removed by applying a carbonate salt, which can penetrate the hair, and then acidifying the hair, thus producing carbon dioxide gas. This gas serves to remove the undesired chemicals, and so remove much of the odor. The carbonate salt is applied in a "flow lotion."

The flow lotion is a water solution of water soluble bicarbonate or carbonate salts at concentrations of 0.1% to saturated aqueous solutions. The preferred concentration is from 1–12%. Examples of the more common water soluble salts are the ammonium, potassium, and sodium bicarbonates/carbonates or mixtures thereof. Other less soluble carbonates such as calcium, lithium, and magnesium can be used as saturated solutions and/or suspensions or in combination with the more soluble salts described above. It is believed that, in theory, any water-soluble bicarbonate/carbonate salt capable of reacting with acids to liberate carbon dioxide can be used.

Ideally, the pH of the bicarbonate/carbonate solution should be close to pH 8 since at this pH the fiber remains swollen and allows penetration of the salts while minimizing fiber damage. In addition, the lower pH requires a lower concentration of acid to liberate carbon dioxide from these salts. The higher the pH, the greater the potential for fiber damage and the greater the amount of acid required to liberate carbon dioxide. Since salts of carbonates are more alkaline than bicarbonates, they should be used at lower concentrations to limit fiber damage caused by highly alkaline materials.

Conditioning reagents exemplified by quaternary ammonium derivatives, amino acids, hydrolyzed collagen, silicones, as well as other cosmetically effective ingredients that are compatible with the formulation can also be added to the "flow lotion" to improve fiber combing characteristics, feel, sheen, elasticity, etc. In addition, emulsifiers, preservatives, fragrances, color, viscosity and foam builders, etc., can also be included as ingredients of the formulation.

These bicarbonate/carbonate solutions/suspensions are applied to the hair fiber after the reduction step as a "flow lotion," that is, after the reducing reagent is removed from the hair by rinsing with water. If the flow lotion is applied before the rinsing step, some improvement in odor removal occurs upon acidification, but not to the same extent as when applied after fiber rinsing. Bicarbonate/carbonate salts can also be included in the waving lotion. However, in this case the hair cannot be rinsed before application of the acid lotion or neutralizer. We have found that this method of application is not as efficacious as when a separate bicarbonate/carbonate flow lotion is applied.

In a similar manner, a waiting period, after application of the bicarbonate/carbonate "flow lotion" and before application of the acid lotion, seems to increase the efficiency of odor removal. This waiting period allows the "flow lotion" to penetrate deep into the fiber. If the bicarbonate/carbonate lotion is applied after the perming procedure is completed (i.e., after neutralization but before rinsing), odor removal is not as effective as when utilized as a flow lotion. It is also possible to use this odor removal procedure on previously permed hair. In this case the bicarbonate/carbonate lotion is applied first, and after a suitable waiting period (i.e., five to ten minutes), the acidic lotion is applied.

The acidic lotion required to release carbon dioxide can consist of organic or inorganic acids at concentrations necessary to react with the bicarbonate/carbonate salts. Examples of organic acids employed are citric, tartaric, acetic, succinic, maleic, and methane sulfonic. Inorganic acids utilized are hydrochloric, sulfuric, phosphoric, etc. Mixtures of organic and inorganic acids may also be used. The only limiting factor is that these acids do not react with scalp and skin in a deleterious manner at use concentrations. These acidic lotions may also contain quaternary ammonium derivatives, amino acids, hydrolyzed collagen, silicones, and other ingredients that will improve conditioning, combing, and appearance of the hair fiber. In addition, emulsifiers, preservatives, fragrances, color, viscosity, and foam builders, etc., can also be included as ingredients of the formulation.

The acidification of bicarbonate/carbonate salts and the oxidation of keratin cysteine to cystine (i.e., neutralization) can be combined into one step. An acidic neutralizer containing 0.5–5% hydrogen peroxide and one of the acids previously described, or mixtures thereof, at a concentration of 0.1–50% can be employed. Preferred concentrations are 2–3% hydrogen peroxide and 5–7% acid. Conditioners such as quaternary ammonium derivatives and silicones as well as other cosmetically effective ingredients that are capable of improving the characteristics of the hair fiber and are compatible with the other ingredients of the formulation can also be added to the neutralizer. In addition, emulsifiers, preservatives, fragrances, color, viscosity, and foam builders, etc., can also be included as ingredients of the formulation.

EXAMPLES

Typical formulations employed in practicing our invention are given in Tables I–IV.

In order to test the efficacy of the present invention, half head testing was performed with both "acid" and "alkaline" based waving lotions. These lotions were unfragranced, and their formulations are summarized in Tables III and IV. Half head testing was performed as follows. A test subject's hair was shampooed with a chelating cleansing shampoo and then water wrapped onto perming rods. After applying the waving lotion to the whole head and allowing the reduction to proceed for a period of 15 to 20 minutes, the waving lotion was removed by rinsing. At this point, a bicarbonate/carbonate flow lotion (i.e., see Table I), was applied to one half of the curlers (i.e., either right or left portion of the head) and allowed to penetrate the fiber for a least five minutes. At the end of this period, the whole head was treated with one of the acid neutralizers formulated as indicated in Table II. After five minutes, the neutralizer was removed by rinsing and a panel of four individuals compared the odor of the two sides of the head. In all cases, the bicarbonate/carbonate flow lotion treated side was preferred unanimously.

Similar experiments were performed in which bicarbonate/carbonate was included in the alkaline waving lotion and the acidic neutralizer was applied, without removing the waving lotion by rinsing with water. Although some odor improvement was noticed on the side permed with the bicarbonate/carbonate waving lotion, it was not as dramatic as the "flow lotion" procedure described above. In addition, the condition of the permed fiber was not as acceptable as with the "flow lotion" treatment.

Half head experiments in which previously permed hair was treated with a bicarbonate/carbonate lotion followed by an acidic, peroxide free, lotion showed some improvement in the removal of post perm malodors. Again this procedure is not as efficacious as the flow lotion treatment.

If a surfactant is added to the "flow lotion," a mild shampooing action occurs which enhances odor removal. This mild shampooing action does not interfere with curl formation and does not relax the contour of the hair as does post perm shampooing. In addition, the foaming action caused by carbon dioxide evolution is enhanced by the surfactant and aids the stylist in identifying which rods have been treated, which minimizes the chance of missing a rod.

Conditioning reagents exemplified by quaternary ammonium derivatives, amino acids, hydrolyzed collagen, silicones, as well as other cosmetically effective ingredients that are compatible with the system can also be added to the "flow lotion" to improve fiber combing characteristics, feel, sheen, etc.

TABLE I

| Ingredient | Flow Lotion Formulations | | | | | | | |
|---|---|---|---|---|---|---|---|---|
| | I | II | III | IV | V | VI | VII | VIII |
| Ammonium Bicarbonate | 50.00 | 50.00 | 20.00 | — | 10.00 | 50.00 | 50.00 | 50.00 |
| Sodium Bicarbonate | — | — | — | 20.00 | — | — | — | — |
| Sodium Lauryl Sulfate | — | 10.00 | 4.00 | 4.00 | — | 10.00 | 10.00 | 10.00 |
| Cocamidopropyl Betaine | — | — | 2.00 | 2.00 | — | — | — | — |
| Ammonium Carbonate | 10.00 | 10.00 | — | — | 2.00 | 10.00 | 10.00 | 10.00 |
| Cetyl Betaine | 5.00 | 5.00 | — | — | 0.30 | 5.00 | 5.00 | 5.00 |
| Katon CG | 0.30 | 0.30 | — | — | — | 0.30 | 0.30 | — |
| Hydroxyethyl Cellulose | 1.00 | 1.00 | — | — | — | — | — | — |
| Polyquaternium-7 | 5.00 | 5.00 | — | — | — | 5.00 | 5.00 | 5.00 |
| Sorbitol | — | — | — | — | 2.00 | — | — | — |

TABLE I-continued

| Ingredient | Flow Lotion Formulations | | | | | | | |
|---|---|---|---|---|---|---|---|---|
| | I | II | III | IV | V | VI | VII | VIII |
| Q2-7224 | — | — | — | — | 0.10 | — | — | — |
| Quaternium-75 | — | — | — | — | 0.10 | — | — | — |
| Phenoxyethanol | — | — | — | — | 0.20 | — | — | — |
| Xanthum Gum | — | — | — | — | — | 0.50 | 2.25 | 1.25 |
| Water q.s. (gms.) | 500 | 500 | 200 | 200 | 100 | 500 | 500 | 500 |

Each column represents a separate formulation. Weights are in grams. Katon CG is a trade name for methylchloroisothiazolinone and methylisothiazolinone. Q2-7224 is a trade name for trimethylsilylamodimethicone, octoxynol 40, isolaureth 6, and propylene glycol. Sodium, potassium, ammonium, calcium, lithium, and magnesium carbonates and/or bicarbonates can be substituted for the above carbonates and bicarbonates by properly adjusting the proportions.

A typical method of mixing a flow lotion is illustrated by the mixing of formula VI or VII. This would be done by:
1. Combine water and xanthan gum. Stir until clear.
2. Add ammonium carbonate, stirring until clear.
3. Add ammonium bicarbonate, stirring until clear.
4. Add the sodium lauryl sulfate with stirring.
5. Add the cetyl betaine while increasing the stirring to insure a uniform mix.
6. Add the polyquaternium-7 and stir until uniform.
7. Add the Kathon CG
8. Make up to final weight with water, stir until uniform.

TABLE II

| | Acid Neutralizer Lotion | | | |
|---|---|---|---|---|
| Ingredient | I | II | III | IV |
| Hydrogen Peroxide (50%) | 23.0 | 23.0 | 23.0 | 23.0 |
| Succinic Acid | 30.0 | — | — | — |
| Phosphoric Acid | — | 25.0 | 12.5 | — |
| Hydrochloric Acid | — | — | — | 15.0 |
| Water q.s (gms) | 500 | 500 | 500 | 500 |

Each column represents a separate formulation. Weights are in grams.

TABLE III

| Acid Waving Lotion - Part A | |
|---|---|
| Glyceryl Thioglycolate (80%) | 95.02% |
| Glycerine | 4.98 |
| Acid Waving Lotion - Part B | |
| Deionized Water | 82.83% |
| Ammonium Thioglycolate (60%) | 7.67 |
| Sodium Lauryl Sulfate | 0.05 |
| Ceteth-20 | 3.00 |
| Quaternium-52 | 0.45 |
| Ammonium Hydroxide (28%) | 5.00 |
| Fragrance | 1.00 |

Percentages are by weight.
Part B is mixed as follows:
1. Combine water and ammonium thioglycolate.
2. Add sodium lauryl sulfate. Stir until all dissolved.
3. Combine Ceteth-20 and fragrance. Melt at 45° C and mix.
4. Combine above with stirring.
5. Add Quaternium-52.
6. Add ammonium hydroxide.
7. Make up to final weight with water. Stir until uniform.

For use, 31.5 grams of Part A are combined with 78.0 grams of Part B.

TABLE IV

| Alkaline Waving Lotion | |
|---|---|
| Deionized Water | 81.10% |
| Ammonium Thioglycolate (60%) | 12.30 |
| PPG-12-PEG-50 Lanolin | 0.10 |
| Lytron 288 | 1.00 |
| Ammonium Hydroxide (28%) | 4.50 |
| Fragrance | 1.00 |

Percentages are by weight.
Lytron 288 is a trade name for DEA-Styrene/Acrylates/DVB Copolymer and Ammonium Nonoxynol-4-sulfate and Diethanolamine.
The alkaline waving lotion can be made up as follows:
1. Combine water and ammonium thioglycolate.
2. Combine PPG-12-PEG-50 lanolin and fragrance.
3. Combine above with stirring.
4. Add the Lytron 288. Stir until uniform.
5. Add the ammonium hydroxide.
6. Make up to final weight with water. Stir until uniform.

We claim:
1. The method of reducing post permanent wave odors from hair, the odors having resulted from a permanent waving treatment which includes a reduction step using a mercaptan reducing solution followed by an oxidation step and rinsing said reducing solution from the hair, said method including the steps of
  treating the hair with an aqueous 0.1 to 50% solution of a salt from the group consisting of water-soluble carbonate salt and water-soluble bicarbonate salts, leaving said aqueous salt solution on the hair for a sufficient time to allow the lotion to penetrate the hair fibers, and
  thereafter treating the hair with an aqueous acid solution which is tolerable by the skin, hair, and scalp to release carbon dioxide gas, said two treatments occurring after the reduction step and before or during the oxidation step, wherein when said acid application and oxidation steps occur simultaneously hydrogen peroxide is contained in said acid solution,
  thereby reducing said odors.
2. The method of claim 1 in which said group of water-soluble carbonate and bicarbonate salts includes sodium, potassium, and ammonium salts.
3. The method of claim 1 in which said group of water-soluble carbonate and bicarbonate salts includes calcium, lithium, and magnesium salts.
4. The method of claim 1 in which said aqueous acid solution is selected from the group consisting of hydrochloric, sulfuric, phosphoric, citric, tartaric, acetic, succinic, maleic, and methane sulfonic acids.

5. The method of claim 1 including using hydrogen peroxide in the step of treating the hair with aqueous acid solution, whereby oxidation of the hair can occur.

6. The method of claim 1 in which the concentration of said salt in said aqueous solution is between about 1% and 12%.

7. The method of claim in which said aqueous solution of salt has a pH of about 8.

8. The method of claim 1 in which the hair is treated with said aqueous solution of salt for a period of about five to ten minutes.

* * * * *